United States Patent

Heuer et al.

[11] Patent Number: 5,972,971
[45] Date of Patent: *Oct. 26, 1999

[54] FUNGICIDAL ACTIVE COMPOUND COMBINATIONS

[75] Inventors: Lutz Heuer, Krefeld; Martin Kugler, Leichlingen; Hans-Ulrich Buschhaus; Heinrich Schrage, both of Krefeld; Franz Kunisch, Odenthal, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/564,249

[22] PCT Filed: Jun. 8, 1994

[86] PCT No.: PCT/EP94/01868

§ 371 Date: Dec. 15, 1995

§ 102(e) Date: Dec. 15, 1995

[87] PCT Pub. No.: WO95/00303

PCT Pub. Date: Jan. 5, 1995

[30] Foreign Application Priority Data

Jun. 21, 1993 [DE] Germany ............... 43 20 495
Mar. 2, 1994 [DE] Germany ............... 44 06 819

[51] Int. Cl.[6] ............... A01N 43/40; A01N 43/653; C07D 249/08; C07D 401/06
[52] U.S. Cl. ............... 514/341; 514/383; 546/272.7; 548/262.2
[58] Field of Search ............... 548/267.8, 262.2; 546/272.7; 514/383, 341

[56] References Cited

U.S. PATENT DOCUMENTS 4,315,017  2/1982  Linhart et al. ............... 424/269
5,196,407  3/1993  Goletz et al. ............... 514/63

FOREIGN PATENT DOCUMENTS 0385076  9/1990  European Pat. Off. .
0458060  11/1991  European Pat. Off. .
0514644  11/1992  European Pat. Off. .
0533017  3/1993  European Pat. Off. .
9406293  3/1994  European Pat. Off. .
0591764  4/1994  European Pat. Off. .
9302557  2/1993  WIPO .

OTHER PUBLICATIONS

Chemicals Abstracts, vol. 118, No. 21, May 24, 1993, Columbus Ohio, US Abstracts No. 207408.
Brighton Crop. Prot. Conf. —Pests Dis., No. 1, 1992 pp. 419–426.

Primary Examiner—Johann Richter
Assistant Examiner—Jane C. Oswecki
Attorney, Agent, or Firm—Sprung Kramer Schaefer & Briscoe

[57] ABSTRACT

The present application relates to new active compound combinations composed, on the one hand, of prior art compounds metaconazole, 5-[(4-chlorophenyl)methyl]-2,2-dimethyl-1-(1H-1,2,4-triazol-1-yl-methyl)cyclopentanol and imidacloprid, 1-[(6-chloro-3-pyridinyl)-methyl]-4,5-dihydro-N-nitro-1H-imidazole-2-amine, and, on the other hand, of other prior-art active compounds, the combinations being extremely suitable for the protection of wood products.

5 Claims, No Drawings

5,972,971

FUNGICIDAL ACTIVE COMPOUND COMBINATIONS

This application is a 371 of PCT/EP94/01868 of Jun. 08, 1994.

The present application relates to new active compound combinations composed, on the one hand, of prior-art α-butyl-α-(2,4-dichlorophenyl)-1H-1,2,4-triazole-1-ethanol (hexaconazole) and/or 5-[(4-chlorophenyl)methyl]-2,2-diethyl-1-(1H-1,2,4-triazol-1-yl-methyl)cyclopentanol (metconazole) and, on the other hand, of further prior-art active compounds, the combinations being extremely suitable for the protection of industrial materials.

It has already been disclosed that α-butyl-α-(2,4-dichlorophenyl)-1H-1,2,4-triazole-1-ethanol (hexaconazole) has fungicidal properties.

Mixtures comprising hexaconazoles have also been disclosed (cf. EP 415 569, GB 2 119 653, EP 95 242, EP 289 356, EP 287 346).

The mixtures are used in the protection of plants and materials.

However, wood preservatives have to meet demands which exceed a simple fungicidal activity.

It was therefore the aim and object of the present invention to find a wood preservative which is highly active against wood-discolouring and wood-destroying fungi and against insects which damage wood, in particular wood-destroying longhorn beetles (Cerambycidae, Lyctidae, Bostrychidae and Anobiidae) including termites and which has a good long-term action, the activity of the fungicide not being adversely affected by the insecticide, or vice versa. Moreover, the wood preservative should have a good penetration capacity in the wood and the derived timber product.

It has been found according to the invention that these aims and objectives are achieved by a composition or concentrate for the preservation of wood and derived timber products which comprises hexaconazole in a mixture with a synergistically acting insecticide.

Preferably, at least one further azole fungicide is additionally added to this mixture.

The invention therefore relates to a wood preservative comprising α-butyl-α-(2,4-dichlorophenyl)-1H-1,2,4-triazole-1-ethanol and at least one synergistically acting insecticide.

Preferred is a wood preservative comprising hexaconazole and at least one synergistically acting insecticide and at least one further azole fungicide.

The wood preservatives comprise 0.01 to 25% by weight of hexaconazole and 0.00001 to 10% by weight of insecticide and, if appropriate, 0.1 to 99.9% by weight of azole fungicide. The wood preservatives furthermore generally comprise over 40% of a mixture of solvent and/or diluent and/or organochemical binder or fixative, processing auxiliaries, colorant, pigment, colorant mixture or pigment mixture.

Azoles which are preferred as components in the mixture are:

Azaconazole:

1-{[2-(2,4-dichlorophenyl)-1,3-dioxolan-2-yl]methyl}1-H-1,2,4-triazole

Propiconazole:

1-[2-(2,4-dichlorophenyl)-4-propyl-1,3-dioxolan-2-yl] methyl-1-H-1,2,4-triazole

Tebuconazole:

1-p-chlorophenyl-4,4-dimethyl-3(1H-1,2,4-triazol-1-yl-methyl)pentan-3-ol

Cypronazole 2-(4-chlorophenyl)-3-cyclopropyl-1-(1H-1,2,4-tiazol-1-yl) butan-2-ol 2-(1-chloro-cyclopropyl)-1-(2-chlorophenyl)-3-(1H-1,2,4-triazol-1yl)-propan-2-ol 2-(tert-butyl)-1-(2-chlorophenyl)-3-(1H-1,2,4-triazol-1-yl) propan-2-ol and/or hexaconazole or metconazole.

Particularly preferred mixtures comprise as azoles, in addition to hexaconazole, tebuconazole, propiconazole, cycproconazole and/or 2-(1-chloro-cyclopropyl)-1-(2-chlorophenyl)-3-1H-(1,2,4-triazol-1-yl)-propan-2-ol, preferably in a ratio by weight to hexaconazole of 1:9 to 9:1.

Other very particularly preferred further fungicidal components in the mixtures are:

bromuconazole, dichlobutrazol, diniconazole, penconazole, methyl (E)methoximino[α-(o-tolyloxy)-o-tolyl)]acetate, methyl (E)-2-{2-[6-(2-cyanophenoxy)pyrimidin-4-yl-oxy] phenyl}-3-methoxyacrylate, methfuroxam, carboxin, fenpiclonil, 4-(2,2-difluoro-1,3-benzodioxol-4-yl)-1H-pyrrole-3-carbonitrile, butenafine and/or 3-iodo-2-propinyl n-butylcarbamate.

The following insecticides are used as synergistic insecticidal components in the mixtures:

phosphoric esters such as azinphos-ethyl, azinphos-methyl. α-1(4-chlorophenyl)-4-(O-ethyl, S-propyl)phosphoryloxy-pyrazole, chlorpyrifos, coumaphos, demeton, demeton-S-methyl, diazinon, dichlorvos, dimethoate, ethoate. ethoprophos, etrimfos, fenitrothion, fenthion, heptenophos, parathion, parathion-methl, phosalone, phoxim, pirimiphos-ethyl, pirimiphos-methyl, profenofosm prothiofos, sulfprofos, triazophos and trichlorphon;

Carbamates, such as aldicarb, bendiocarb, α-2-(1-methylpropyl)-phenyl methylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

Organisilicon compounds, preferably dimethyl(phenyl)silyl-methyl 3-phenoybenzyl ethers, such as dimethyl-(4-ethoxyphenyl)silylmethyl 3-phenoxybenzyl ether, or (dimethylphenyl)-silyl-methyl 2-phenoxy-6-pyridylmethyl ethers, such as, for example, dimethyl-(9-ethoxy-phenyl)-silylmethyl 2-phenoxy-6-pyridylmethyl ether or [(phenyl)-3-(3-phenoxyphenyl)-propyl](dimethyl)-silanes, such as, for example, (4-ethoxyphenyl)-[3-(4-fluoro-3-phenoxyphenyl-propyl]dimethyl-silane, sila fluofin, Pyrethroids, such as allethrin, alphamethrin, bioresmethrin, byfenthrin, cycloprothin, cyfluthrin, decamethrin, cyhalothrin, cypermethrin, deltamethrin, alpha-cyano-3-phenyl -2-methylbenzyl 2,2-dimethyl-3-(2-chloro-2-trifluoro-methylvin yl)cyclopropane-carboxylate, fenpropathrin, fenfluthrin, fenvalerate, flucythrinate, flumethrin, fluvalinate, permethrin, resmethrin and tralom-ethrin;

Nitroimines and nitromethylenes, such as 1-[(6-chloro-3-pyridinyl)-methyl]-4,5-dihydro-N-nitro-1H-imidazole-2-amine (imidacloprid), N-[(6-chloro-3-pyridyl)methyl-]$N^2$-cyano-$N^1$-methylacetamide (NI-25), Abamectin, AC 303,630, acephate, acrinathrin, alanycarb, aldoxycarb, aldrin, ammonium bifluoride, amitraz, azamethiphos, *Bacillus thuringiensis*, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, O-2-tert-butyl-pyrimidin-5-yl o-isopropyl phosphorothiate, thiocyclam, thiofanox, thiometon, tralomethrin, triflumuron, trimethacarb, vamidothion, Verticillium Lacanii, XMC, xylylcarb, benfuracarb, bensultap, bifenthrin bioallethrin, MER bioallethrin (S)-cyclopentenyl isomer, bromophos, bromophos-ethyl, buprofezin, cadusafos, calcium polysulphide, carbophenothion, cartap, quinomethionate, chlordane, chlorfenvinphos, chlorfltazuron, chlormephos, chloropicrin, chlorpyrifos, cyanophos, beta-cyfluthrin, alpha-cypermethrin, cyophenothrin, cyromazine, dazomet, DDT, demeton-S-methyl sulphone, diafenthiuron, dialifos, dicrotophos, diflubenzuron, dinoseb, dioxabenzofos, diaxacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mecarbam, mephosfolan, mercurous, chloride, metam, metarthizium, anisopliae, methacrifos, methamidophos, methidathion, methiocarb, methoprene, methoxychlor, methyl isothiocyanate, metholcarb, mevinphos, monocrotophos, Naled, Neodiprion sertifer NPV, nicotine, omethoate, oxydemeton-methyl, pentachlorophenol, petroleum oils, phenothrin, phenthoate, phorate;

Particularly preferred insecticides are:
Chlorpyrifos, phoxim, silafluofen, cyfluthrin, cypermethrin, deltamethrin, permethrin, imidacloprid, hexaflumuron, lindane.

The synergistic action of the mixtures is observed at mixing ratios from 99:1 to 1:99, preferably from 3:1 to 1:3, and very particularly preferably in a ratio of 1:1.

The mixtures according to the invention which have thus been prepared are active not only against fungi, but also against insects which destroy materials.

In general, the insecticides are present at a rate of 0.00001% to 10%, preferably 0.0001% to 5%, particularly preferably 0.001% to 1%.

To achieve even further increased activity against wood-destroying fungi, it is also possible to additionally admix the following fungicides:

Triazoles:
amitrole, azocyclotin, BAS 480F, bitertanol, difenoconazole, fenbuconazole, fenchlorazole, fenethanil, fluquinconazole, flusilazole, flutriafol, imibenconazole, isazofos, myclobutanil, opus, paclobutrazol, ±)-cis-1-(4-chlorophenyl)-2-(1H-1,2,4 -triazol-1-yl)-cycloheptanol, tetraconazole, triadimefon, triadimenol, triapenthenol, triflumizole, uniconazole;

Imidazoles:
imazalil, pefurazoate, prochloraz, triflumizole, 2-(1-tert-butyl)-1-(2-chlorophenyl)-3-(1,2,4-triazol-1-yl)-propan-2-ol, thiazolcarboxanilides, such as 2',6'-dibromo-2-methyl-4-trifluoromethoxy-4'-trifluoromethyl-1,3-thiazole-5-carboxanilide.

Copper salts:
Copper, sulphate, copper carbonate, copper chloride, copper ammonia complexes, copper amine complexes.

Zinc salts:
Zinc sulphate, zinc carbonate, zinc chloride.

Mixed salts:
Copper/boron mixtures, copper/chromium/boron mixtures, copper/chromium/arsenic mixtures.

Methyl (E)-2-[2-[6-(2-cyanophenoxy)pyrimidin-4-yloxy]phenyl]3-methoxyacrylate, methyl(E)-2-[2-[6-(2-thioamidophenoxy)pyrimidin-4-yloxy]phenyl]-3-methoxyacrylate, methyl (E)-2-[2-[6-(2-fluorophenoxy)pyrimidin-4yloxy]phenyl]-3-methoxyacrylate, methyl (E)-2-[2-[6-(2,6-difluorophenoxy)pyrimidin-4-yloxy]-phenyl]-3-methoxyacrylate, methyl (E)-2-[2-[3-(pyrimidin-2-yloxy]phenoxy]-phenyl]-3-methoxyacrylate, methyl (E)-2-[3-[5-(methylpyrimidin-2-yloxy]-phenoxy]phenyl]-3-methoxyacrylate, methyl(E)-2-[2-[3-(phenyl-sulfonyloxy)phenoxy]phenyl]-3-methoxyacrylate, methyl (E)-2-[3-[4-(nitrophenoxy)phenoxy]-phenyl]-3-methoxyacrylate, methyl (E)-2-[2-phenoxyphenyl]-3-methoxyacrylate, methyl (E)-2-[2-(3,5-dimethylbenzoyl)pyrrol-1-yl]3-methoxyacrylate, methyl (E)-2-[2-(3-methoxyphenoxy)phenyl]-3-methoxyacrylate, methyl (E)-2-[2-(2-(phenyl-ethen-1-yl)phenyl]-3-methoxyacrylate, methyl (E)-2-[2-(3,5-dichlorophenoxy)-pyridin-3-yl]3-methoxyacrylate, methyl (E)-2-(2-(3-(1,1,2,2-tetrafluoroethoxy)-phenoxy)phenyl)-3-methoxyacrylate, methyl (E)-2-(2-[3-alpha-hydroxybenzyl)-phenoxy]phenyl)3-methoxyacrylate, methyl (E)-2-(2-(4-(phenoxypyridin-2-yloxy)-phenyl)-3-methoxyacrylate, methyl (E)-2-[2-(3-n-propyloxyphenoxy)-phenyl]-3-methoxyacrylate, methyl (E)-2-[2-[3-(isopropyloxyphenoxy)phenyl]-3-methoxy-acrylate, methyl (E)-2-[2-[3-(2-fluorophenoxy)phenoxy]phenyl]-3-methoxyacrylate, methyl (E)-2-[2-(3-ethoxyphenoxy)phenyl]-3-methoxyacrylate, methyl(E)-2-[2-(4-tert.butylpyridin-2-yloxy)phenyl]-3-methoxyacrylate, methyl (E)-2-[2-[3-(3-cyanophenoxy)phenoxy]phenyl]-3-methoxyacrylate, methyl (E)2-[2-(3-methylpyridin-2-yloxymethyl)phenyl]-3-methoxyacrylate, methyl (E)-2-[2-[6-(2-met hylphenoxy)-pyridin-4-yloxy]phenyl]-3-methoxyacrylate, methyl (E)-2-[2-(5-bromopyridin-2-yloxymethyl]phen yl]-3-methoxyacrylate, methyl (E)-2-[2-(3-(3-iodopyridin-2-yloxy]phenoxy)phen yl]-3-methoxyacrylate, methyl (E)-2-[2-[6-(2-chloropyridin-3-yloxy]pyrimidin-4-yl oxy]phenyl]-3-methoxyacrylate, (E), (E) methyl-2-[2-(5,6-dimethylpyrazin-2-ylmethyloximino methyl)phenyl]-3-methoxyacrylate, (E) methyl-2-{2-[6-[6-methylpyridin-2-yloxy)pyrimidin-4yloxy)phenyl}-3-methoxyacrylate, (E),(E)methyl-2-{2-(3-methoxyphenyl) methyloximino methyl)phenyl}-3-methoxyacrylate, (E) methyl-2-{2-(6-(2-azidophenoxy)pyrimidin-4-yloxy]phenyl}3-methoxyacrylate, (E),(E)methyl-2-{2-[6-phenylpyrimidin-4-yl)methyloximino methyl)phenyl}-3-methoxyacrylate, (E),(E)methyl-2-{2-[(4-cglorophenyl)-methyloximinomethyl]phenyl}-3-methoxyacrylate, (E)methyl-2-{2-[6-(2-n-propylphenoxy)1,3,5-triazin-4-yloxy]phenyl}-3-methoxyacrylate, (E),(E)methyl-2-{2-[(3-nitrophenyl)methyloximnino methyl)phenyl}-3-methoxyacrylate.

Succinate dehydrogenase inhibitors, such as:
fenfuram, furcarbanil, cyclafluramid, furmecyclox, Seedvax, metsulfovax, pyrocarbolid, oxycarboxin, shirlan, mebenil (mepronil), benodanil, flutolanil (Moncut)

Naphthalene derivatives, such as:
terbinafine, naftifine, butenafine, 3-chloro-7-(2-aza-2,7,7-trinmethyl-oct-3-en-5-ine)

Sulfenamides such as dichlorofluanid, tolylfluanid, folpet, fluorfolpet; captan, captofol, Benzimidazoles such as carbendazim, benomyl, furathiocarb, fuberidazole, thiophonatmethyl, thiabendazole or their salts;

Thiocyanates, such as thiocyanatomethylthiobenzothiazole, methylene bisthiocyanate;

Quaternary ammonium compounds, such as benzyldimethyltetradecylammonium chloride, benzyldimethldodecylammonium chloride, didecyldimethylammonium chloride, Morpholine derivatives, such as tridemorph, fenpropimorph, falimorph, dimethomorph, dodemorph; aldimorph, fenpropidin and their aryl sulphonic acid salts, such as, for example, p-toluenesulfonic acid and p-dodecylphenylsulphonic acid, Iodine derivatives, such as diiodomethyl p-tolyl sulphone, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 6iodo-3-oxo-hex-5-in-ol butylcarbamate, 6-iodo-3-oxo-hex-5-in-ol phenylcarbamate, 3-iodo-2-propinyl n-hexylcarbamate, 3-iodo-2-propinyl cyclohexylcarbamate, 3-iodo-2-propinyl phenylcarbamate;

Phenol derivatives, such as tribromophenol, tetrachlorophenol, 3-methyl-4-chlorophenyl, dichlorophen, o-phenylphenol, m-phenylphenol, p-phenylphenol, 2-benzyl-4-chlorophenol;

Glutaraldehyde;

Bromine derivatives, such as 2-bromo-2-nitro-1,3-propanediol;

Isothiazolinones, such as N-methylisothiazolin-3-one, 5-chloro-N-methyl-isothiazolin-3-one, 4,5-dichloro-N-octyliso-thiazolin-3-one, N-octyl-isothiazolin-3-one; Benzoisothiazolinones, 4,5-trimethylene-isothiazolinones;

Pyridines or pyrimidines, such as 1-hydroxy-2-pyridinethione (and their sodium, iron, manganese and zinc salts), tetrachloro-4-methylsulphonylpyridine, pyrimethanil, mepanipyrim, dipyrithione;

Metal soaps, such as tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate and zinc benzoate;

Oxides, such as tributyltin oxide, $Cu_2O$, CuO, ZnO;

Dialkyldithiocarbamates, such as sodium and zinc salts of dialkyldithiocarbamates, tetramethylthiuram disulphide;

Dithiocarbamate, cufraneb, ferbam, mancopper, mancozeb, maneb, metam, metiram, thiram zineb, ziam:

Nitriles, such as 2,4,5,6-tetrachloroisophthalodinitrile, 2,3,5,6-tetrafluoroterephthalodinitrile;

Benzothiazoles, such as 2-mercaptobenzothiazole;

Quinolines, such as 8-hydroxyquinoline, and their Cu salts;

Benzamides, such as 2,6-dichloro-N-(4-trifluoromethylbenzyl)-benzamide (XRD-563);

Boron compounds, such as boric acid, boric esters, borax;

Formaldehyde and formaldehyde-releasing compounds, such as benzyl alcohol mono(poly)hemiformal, oxazolidines, hexa-hydro-S-triazines, N-methylolchloroacetamide, paraformaldehyde, nitropyrin, oxolin acid, tecloftalam;

Tris-N-(cyclohexyldiazeniumdioxy)-aluminium, N-(cyclohexyldiazeniumdioxy)-tributyltin or potassium salts, bis-N-(cyclohexyldiazeniundioxy)-copper.

Other highly effective mixtures are furthermore prepared with the following active compounds:

Fungicides acypetacs, 2-aminobutane, ampropylfos, anilazine, benalaxyl, bupirimate, quinomethionate, chloroneb, chlozolinate, cymoxanil, dazomet, diclomezine, dichloram, diethofencarb, dimethirimol, dinocab, dithianon, dodine, drazoxolon, edifenphos, ethirimol, etridiazole, fenarimol, fenitropan, fentin acetate, fentin hydroxide, ferimzone, fluazinam, fluromide, flusulfamide, flutriafol, fosetyl, fthalide, furalaxyl, guazatin, hymexazol, iprobenfos, iprodione, isoprothiolane, metalaxyl, methasulfocarb, nitrothal-isopropyl, nuarimol, ofurace, oxadiyl, perflurazoate, pencycuron, phosdiphen, pimaricin, piperalin, procymidone, propamocarb, propineb, pyrazophos, pyrifenox, pyroquilon, quintozene, tar oils, tecnazene, thicyofen, thiophanate-methyl, tolclofos-methyl, triazoxide, trichiamide, tricyclazole, triforine, vinclozolin.

Surprisingly, these combinations of active substances display a particularly powerful microbicidal, in particular fungicidal, activity combined with a wide spectrum of action against microorganisms and insects which are relevant in the protection of materials; they act mainly against moulds, wood-discolouring and wood-destroying fungi and insects. The following groups of microorganisms may be mentioned by way of example, but not by way of limitation:

A: Wood-discolouring fungi:
  A1: Ascomycetes
    Ceratocystis, such as Ceratocystis minor
  A2: Deuteromycetes:
    Aspergillus, such as *Aspergillus niger*
    Aureobasidium, such as *Aureobasidium pullulans*
    Dactylium, such as *Dactylium fusarioides*
    Penicillium, such as *Penicillium brevicaule* or Penicillium variabile
    Sclerophoma, such as *Sclerophoma pithyophila*
    Scopularia, such as *Scopularia phycomyces*
    Trichoderma, such as *Trichoderma viride* or *Trichoderma lignorum*
  A3: Zygomycetes:
    Mucor, such as *Mucor spinorus*
B: Wood-destroying fungi:
  B1: Ascomycetes:
    Chaetomium, such as *Chaetomium globosum* or *Chaetomium alba-arenulum*
    Humicola, such as *Humicola grisea*
    Petriella, such as *Petriella setifera*
    Trichurus, such as *Trichurus spiralis*
  B2: Basidiomycetes:
    Coniophora, such as *Coniophora puteana*
    Coriolus, such as *Coriolus versicolor*
    Donkioporia, such as *Donkioporia expansa*
    Glenospora, such as *Glenospora graphii*
    Gloeophyllum, such as *Gloeophyllum abietinum* or *Gloeophyllum adoratum* or *Gl. protactum* or *Gloeophyllum sepiarium* or *Gl. trabeum*
    Lentinus, such as *Lentinus cyathiformes* or *Lentinus edodes*, such as *Lentinus lepideus* or *Lentinus grinus* or *L. squarrolosus*
    Paxillus, such as *Paxillus panuoides*
    Pleurotus, such as *Pleurotus ostreatus*
    Poria, such as *Poria monticola* or *Poria placenta* or *Poria vaillantii* or *Poria vaporaria*
    Serpula, such as *Serpula himantoides* or *Serpula lacrymans*
    Stereum, such as *Stereum hirsutum*
    Tyromyces, such as *Tyromyces palustris*
  B3: Deuteromycetes
    Alternaria, such as *Alternaria tenius*
    Cladosporium, such as *Clasdosporium herbarum*
C. Wood-destroying insects, such as
  C1: Beetles
    *Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec. Tryptodendron spec. Apate monochus, Bostrychus capucins, Heterobostrychus brunneus, Sinoxylon spec. Dinoderus minutus*
  C2: Hymenoptera
    *Sirex juvencus, Urocerus gigas, Urocerus gigas taignus, Urocerus augur*
  C3: Termites
    *Kalotermes flavicollis, Cryptotermers brevis, Heterotermes indicola, Reticulitermes flavipes, Reticulitermes santonensis, Reticulitermes lucilugus, Mastotermes darwiniensis, Zootermopsis nevadensis, Coptotermes formosanus.*

The amount of the compositions or concentrates employed depends on the species and the occurrence of the insects, microorganisms, the microbial count and the medium. The optimum amount to be applied can be determined by test series upon use. However, in general it suffices to employ 0.001 to 20% by weight, preferably 0.05 to 10% by weight, of the active compound mixture based on the material to be protected.

The active compound mixture can be used as such in the form of concentrates or generally customary formulations, such as solutions, suspensions, emulsions or pastes.

The abovementioned formulations can be prepared in a manner known per se, for example by mixing the active compounds with solvents or diluents, emulsifier, dispersant and/or binder and/or fixative, water repellant, if appropriate desiccants and UV stabilizers and, if appropriate, colorants and pigments and other processing auxiliaries.

The solvent and/or diluent used is an organochemical solvent or solvent mixture and/or an oily or oil-type organochemical solvent or solvent mixture with low volatility and/or a polar organochemical solvent or solvent mixture and/or water and at least one emulsifier and/or wetting agent, or is composed thereof.

Organochemical solvents which are preferably employed are oily or oil-type solvents with an evaporation number of above 35 and a flash point of above 30° C., preferably above 45° C. Suitable mineral oils or their aromatic fractions or mineral-oil-containing solvent mixtures, preferably white spirit, petroleum and/or alkylbenzene, are used as such oily and oil-type solvents which have low volatility and are insoluble in water.

Substances which are advantageously used are mineral oils with a boiling range of 170 to 220° C., white spirit with a boiling range from 170 to 220° C., spindle oil with a boiling range of 250 to 350° C., petroleum or aromatics with a boiling range of 160 to 280° C., oil of turpentine and the like.

In a preferred embodiment, liquid aliphatic hydrocarbons with a boiling range from 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility with an evaporation number of above 35 and a flash point of above 30° C., preferably above 45° C., can be replaced in part by organochemical solvents of high or moderate volatility, with the proviso that the solvent mixture also has an evaporation number of above 35 and a flash point of above 30° C., preferably above 45° C., and that the insecticide/fungicide mixture is soluble or emulsifiable in this solvent mixture.

In a preferred embodiment, some of the organochemical solvent or solvent mixture or an aliphatic polar organochemical solvent or solvent mixture is replaced. Substances which are preferably used are aliphatic organochemical solvents containing hydroxyl and/or ester and/or ether groups, such as, for example, glycol ether, esters or the like.

Particularly suitable as a solvent or diluent is also water, if appropriate in the form of a mixture with one or more of the abovementioned organochemical solvents or diluents, emulsifiers and dispersants.

Particularly preferred are that compositions which are free from aromatic oxyalcohols.

Organochemical binders which are used within the scope of the present invention are the synthetic resins and/or binding drying oils which are known per se and which can be diluted with water and/or dissolved or dispersed or emulsified in the organochemical solvents employed, in particular binders composed of or comprising an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone, silicone resin, drying vegetable and/or drying oils and/or physically drying binders based on a natural and/or synthetic resin.

The synthetic resin used as the binder can be employed in the form of an emulsion, dispersion or solution. Bitumen or bituminous substances can also be used as binders, up to 10% by weight. In addition, colorants, pigments, water repellents, odour-masking agents, inhibitors or corrosion inhibitors and the like, which are known per se, can be employed.

The composition or concentrate preferably comprises according to the invention at least one alkyd resin or modified alkyd resin and/or a drying vegetable oil as the organochemical binder. Substances which are preferably used according to the invention are alkyd resins with an oil content of over 45% by weight, preferably 50 to 68% by weight.

Some or all of the abovementioned binder can be replaced by a fixative (fixative mixture) or a plasticizer (plasticizer mixture). These additives are intended to prevent volatilization of the active compounds or crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or high-molecular-weight glycol ethers, the glycerol esters and the p-toluenesulphonic esters.

Chemically, fixatives are based on polyvinyl alkyl ethers, for example polyvinyl methyl ether, or ketones, such as benzophenone or ethylenebenzophenone.

Wood which can be protected by the active compound mixture according to the invention, or compositions comprising the active compound mixture according to the invention, is to be understood as meaning, for example, structural timber, wooden beams, railway sleepers, bridge components, jetties, vehicles made of wood, boxes, pallets, containers, telephone poles, wood laggings, windows and doors made of wood, plywood, particle board, joiner's work or derived timber products which are quite generally used in construction work or in building joinery.

A particularly effective protection of wood is achieved by large-scale impregnating processes, for example vacuum, double-vacuum or pressure processes.

The microbicidal compositions or concentrates used for the protection of wood and derived timber products comprise the active compound combination at a concentration of 0.01 to 95% by weight, in particular 0.01 to 60% by weight.

Preferred compositions (ready-to-use compositions) preferably comprise 0.2 to 3% by weight, in particular 0.5 to 2% by weight, of hexaconazole as a mixture with the other azole, 0.005 to 1% by weight, preferably 0.01 to 0.5% by weight, of the insecticide and at least one organochemical solvent or solvent mixture and/or one oily or oil-type organochemical solvent or solvent mixture of low volatility and/or one polar organochemical solvent or solvent mixture and/or water and emulsifier and/or wetting agent and, if appropriate, 0 to 5% by weight, preferably 0.1 to 3% by weight, of fixative and/or other components as the remainder.

Particularly preferred (ready-to-use) compositions comprise 2 to 30% by weight, preferably 5 to 22% by weight, calculated as a solid, of a synthetic resin binder, preferably an alkyd resin and/or a drying vegetable oil and at least one organochemical solvent or solvent mixture and/or one oily or oil-type organochemical solvent or solvent mixture of low volatility and/or one polar organochemical solvent or solvent mixture and/or water and emulsifier and/or wetting agent and, if appropriate, desiccants, colorants, pigments, antisettling agents and/or UV stabilizers as the remainder.

Concentrates for preserving wood and derived timber product preferably comprise 0.2 to 25% by weight, preferably 3 to 8% by weight, of hexaconazole in a mixture with the other azole, 0.05 to 5% by weight, preferably 0.5 to 1% by weight, of the insecticide, 5 to 40% by weight, preferably 10 to 30% by weight (calculated as a solid) of at least one organochemical binder and/or fixative or plasticizer, and additionally an organochemical solvent or solvent mixture and/or an oily or oil-type organochemical solvent or solvent mixture of low volatility and/or a polar organochemical solvent or solvent mixture and/or a penetrant and/or water and an emulsifier and/or wetting agent as the remainder.

Particularly preferred compositions of the concentrations comprise the other azoles from 0 to 50% by weight, preferably 0.5 to 25% by weight (based on 100% by weight), of hexaconazoles employed.

The compositions according to the invention advantageously allow the prior-art microbicidal compositions to be replaced by more effective ones. They have good stability and an advantageous, broad spectrum of action.

We claim:

1. A wood preservative composition comprising a wood preservative effective amount of a synergistic combination of:
   a) 5-[(4-chlorophenyl)methyl]-2,2-dimethyl-1-(1H-1,2,4-triazol-1-yl-methyl)cyclopentanol (metconazole) or an acid addition salt or metal complex thereof; and
   b) 1-[(6-chloro-3-pyridinyl)-methyl]-4,5-dihydro-N-nitro-1H-imidazole-2-amine (imidacloprid) or an acid addition salt or metal complex thereof.

2. A wood preservative composition according to claim 1, which further comprises another azole fungicide besides metconazole.

3. A wood preservative composition according to claim 2, wherein the other azole fungicide is selected from the group consisting of:
   a) α-butyl-α-(2,4-dichlorophenyl)-1H-1,2,4-triazole-1-ethanol (hexaconazole) or an acid addition salt or metal complex thereof;
   b) 1-{[2-(2,4-dichlorophenyl)-1,3-dioxolan-2-yl]methyl}-1H-triazole (azaconazole) or an acid addition salt or metal complex thereof;
   c) 1-[2-(2,4-dichlorophenyl)-4-propyl-1,3-dioxolan-2-yl]methyl-1H-1,2,4-triazole (propiconazole) or an acid addition salt or metal complex thereof;
   d) 1-(4-chlorophenyl)-4,4-dimethyl-3-(1H-1,2,4-triazol-1-ylmethyl)pentan-3-ol (tebuconazole) or an acid addition salt or metal complex thereof;
   e) 2-(4-chlorophenyl)-3-cyclopropyl-1-(1H-1,2,4-triazol-1-yl)butan-2-ol (cyproconazole) or an acid addition salt or metal complex thereof;
   f) 2-(1-chloro-cyclopropyl)-1-(2-chlorophenyl)-3-(1H-1,2,4-triazol-1-yl)-propan-2-ol or an acid addition salt or metal complex thereof; and
   g) 2-(tert-butyl)-1-(2-chlorophenyl)-3-(1H-1,2,4-triazol-1-yl)-propan-2-ol or an acid addition salt or metal complex thereof.

4. A wood preservative composition according to claim 3, which comprises:
   a) 0.01 to 25% by weight of metconazole or an acid addition salt or metal complex thereof;
   b) 0.00001 to 10% by weight of imidacloprid or an acid addition salt or metal complex thereof; and
   c) 0.01 to 25% by weight of hexaconazole or an acid addition salt or metal complex thereof.

5. A method for preserving wood or timber products derived from wood, said method comprising applying to said wood or timber products a wood preservative effective amount of a wood preservative composition according to any one of claims 1–4.

* * * * *